(12) United States Patent
Tang et al.

(10) Patent No.: US 9,983,667 B2
(45) Date of Patent: May 29, 2018

(54) METHOD AND APPARATUS FOR DISPLAY CONTROL, ELECTRONIC DEVICE

(71) Applicant: Xiaomi Inc., Beijing (CN)

(72) Inventors: Mingyong Tang, Beijing (CN); Huayijun Liu, Beijing (CN); Tao Chen, Beijing (CN)

(73) Assignee: Xiaomi Inc., Beijing (CN)

( * ) Notice: Subject to any disclaimer, the term of this patent is extended or adjusted under 35 U.S.C. 154(b) by 17 days.

(21) Appl. No.: 15/074,309

(22) Filed: Mar. 18, 2016

(65) Prior Publication Data
US 2016/0291693 A1    Oct. 6, 2016

(30) Foreign Application Priority Data
Mar. 31, 2015  (CN) .......................... 2015 1 0150291

(51) Int. Cl.
*G09G 5/00*  (2006.01)
*G06F 3/01*  (2006.01)
(Continued)

(52) U.S. Cl.
CPC ............ *G06F 3/013* (2013.01); *A61B 3/0025* (2013.01); *A61B 3/103* (2013.01); *G02B 27/017* (2013.01); *G02B 27/0172* (2013.01); *G06T 3/40* (2013.01); *G09G 3/003* (2013.01); *G09G 5/14* (2013.01); *G02B 2027/014* (2013.01);
(Continued)

(58) Field of Classification Search
CPC .............. G06F 3/013; G06F 3/011; G06F 2203/04806; G06F 7/08; G06F 3/147; G06T 3/40; G06T 11/00; G06T 11/003; G06T 5/009; G06T 5/50; A61B 3/0025; A61B 3/103; G02B 27/0172; G02B 2027/0178; G02B 2027/014; G02B 27/017; G09G 3/003; G09G 5/14; G09G 2340/0407; G09G 2320/0261; G09G 2340/12; G09G 2320/0626;
(Continued)

(56) References Cited

U.S. PATENT DOCUMENTS 6,731,326 B1    5/2004  Bettinardi
2002/0071047 A1    6/2002  Strong et al.
(Continued)

FOREIGN PATENT DOCUMENTS

CN    103886622 A    6/2014
CN    103914151 A    7/2014
(Continued)

OTHER PUBLICATIONS

International Search Report (including English translation) issued in corresponding International Application No. PCT/CN2015/088685, dated Dec. 23, 2015, 6 pages.
(Continued)

*Primary Examiner* — Xilin Guo

(57) ABSTRACT

A method and an apparatus are provided for display control. In the method, the electronic device acquires an image including one or more observed objects. The electronic device determines whether an observed object is clearly visible for a user according to vision information of the user. When determining that the observed object is not clearly visible for the user, the electronic device displays an enlarged image including at least a portion of the observed object.

16 Claims, 8 Drawing Sheets

(51) Int. Cl.
*G09G 3/00* (2006.01)
*G09G 5/14* (2006.01)
*G02B 27/01* (2006.01)
*A61B 3/00* (2006.01)
*A61B 3/103* (2006.01)
*G06T 3/40* (2006.01)
*G09G 3/36* (2006.01)

(52) U.S. Cl.
CPC ....... *G02B 2027/0178* (2013.01); *G09G 3/36* (2013.01); *G09G 2320/0261* (2013.01); *G09G 2340/045* (2013.01); *G09G 2340/12* (2013.01); *G09G 2340/14* (2013.01); *G09G 2354/00* (2013.01)

(58) Field of Classification Search
CPC .................... H04M 1/72594; H04M 2250/12; H04N 3/09; H04N 5/2176
See application file for complete search history.

(56) References Cited

U.S. PATENT DOCUMENTS

| | | | |
|---|---|---|---|
| 2005/0162512 | A1 | 7/2005 | Seakins |
| 2011/0299034 | A1* | 12/2011 | Walsh ............... A61B 3/102 351/206 |
| 2014/0267284 | A1 | 9/2014 | Blanche et al. |
| 2014/0361984 | A1 | 12/2014 | Kim et al. |
| 2016/0035136 | A1* | 2/2016 | Sendai ............... G02B 27/0172 345/633 |
| 2016/0231411 | A1* | 8/2016 | Kumar ............... G06T 7/20 |
| 2016/0320622 | A1* | 11/2016 | Yoshida ............... G06F 3/14 |

FOREIGN PATENT DOCUMENTS

| | | |
|---|---|---|
| CN | 104238739 A | 12/2014 |
| CN | 104407437 A | 3/2015 |
| CN | 104699250 A | 6/2015 |
| EP | 2813922 A1 | 12/2014 |
| JP | H9-101477 A | 4/1997 |
| JP | H10-191204 A | 7/1998 |
| JP | 2001-290571 A | 10/2001 |
| JP | 2005-6897 A | 1/2005 |
| JP | 2006-23953 A | 1/2006 |
| JP | 2009-181324 A | 8/2009 |
| JP | 2011-069849 A | 4/2011 |
| JP | 2012-73940 A | 4/2012 |
| JP | 2015-022580 A | 2/2015 |
| KR | 20110070087 A | 6/2011 |
| KR | 20120020892 A | 3/2012 |
| KR | 20140144510 A | 12/2014 |
| WO | 0246907 A2 | 6/2002 |
| WO | 2011158511 A1 | 12/2011 |
| WO | 2014174168 A1 | 10/2014 |

OTHER PUBLICATIONS

Written Opinion of International Searching Authority (including English translation) issued in corresponding International Application No. PCT/CN2015/088685, dated Dec. 23, 2015, 8 pages.

Extended European Search Report issued in corresponding EP Application No. 15200501, dated Apr. 29, 2016, 10 pages.

Office Action (including English translation) issued in corresponding Korean Patent Application No. 10-2016-7008479, dated Apr. 19, 2017, 15 pages.

First Office Action (including English translation) issued in corresponding Chinese Patent Application No. 201510150291.7, dated Mar. 28, 2017, 17 pages.

Notification of Reasons for Refusal (including English translation) issued in corresponding Japanese Patent Application No. 2016-521986, dated Sep. 12, 2017, 7 pages.

* cited by examiner

METHOD AND APPARATUS FOR DISPLAY CONTROL, ELECTRONIC DEVICE

CROSS-REFERENCE TO RELATED APPLICATIONS

This application is based upon and claims priority to Chinese Patent Application Serial No. 201510150291.7, filed on Mar. 31, 2015, the entire contents of which are incorporated herein by reference.

TECHNICAL FIELD

The present disclosure generally relates to a field of smart device technology, and more particularly, to a method and an apparatus for display control, and an electronic device.

BACKGROUND

With the development of science and technology, there are more and more wearable devices, such as smart bracelets, smart glasses. Then how to fully make use of the hardware characteristic of these wearable devices to facilitate the daily life of people has become an urgent problem to be solved.

SUMMARY

Embodiments of the present disclosure provide a method and an apparatus for display control so as to solve the problems existing in the related art.

According to a first aspect of embodiments of the present disclosure, there is provided a method for display control. In the method, an electronic device determines whether an observed object is clearly visible for a user according to vision information of the user. When determining that the observed object is not clearly visible for the user, the electronic device displays an enlarged image including at least a portion of the observed object.

According to a second aspect of embodiments of the present disclosure, there is provided an apparatus for display control. The apparatus includes: a determining unit and a displaying unit. The determining unit configured to determine whether an observed object is clearly visible for a user according to vision information of the user. The displaying unit is configured to display an enlarged image including at least a portion of the observed object when determining that the observed object is not clearly visible for the user.

According to a third aspect of embodiments of the present disclosure, there is provided an electronic device. The electronic device includes: a processor and a memory for storing instructions executable by the processor. The processor is configured to determine whether an observed object is clearly visible for a user according to vision information of the user. When determining that the observed object is not clearly visible for the user, the processor is configured to display an enlarged image including at least a portion of the observed object.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate embodiments consistent with the invention and, together with the description, serve to explain the principles of the invention.

DETAILED DESCRIPTION

Reference will now be made in detail to exemplary embodiments, examples of which are illustrated in the accompanying drawings. The following description refers to the accompanying drawings in which the same numbers in different drawings represent the same or similar elements unless otherwise represented. The implementations set forth in the following description of exemplary embodiments do not represent all implementations consistent with the invention. Instead, they are merely examples of apparatuses and methods consistent with aspects related to the invention as recited in the appended claims.

The terminology used in the present disclosure is for the purpose of describing exemplary embodiments only and is not intended to limit the present disclosure. As used in the present disclosure and the appended claims, the singular forms "a," "an" and "the" are intended to include the plural forms as well, unless the context clearly indicates otherwise. It shall also be understood that the terms "or" and "and/or" used herein are intended to signify and include any or all possible combinations of one or more of the associated listed items, unless the context clearly indicates otherwise.

It shall be understood that, although the terms "first," "second," "third," etc. may include used herein to describe various information, the information should not be limited by these terms. These terms are only used to distinguish one category of information from another. For example, without departing from the scope of the present disclosure, first information may include termed as second information; and similarly, second information may also be termed as first information. As used herein, the term "if" may include understood to mean "when" or "upon" or "in response to" depending on the context.

Reference throughout this specification to "one embodiment," "an embodiment," "exemplary embodiment," or the like in the singular or plural means that one or more particular features, structures, or characteristics described in connection with an embodiment is included in at least one embodiment of the present disclosure. Thus, the appearances of the phrases "in one embodiment" or "in an embodiment," "in an exemplary embodiment," or the like in the singular or plural in various places throughout this specification are not necessarily all referring to the same embodiment. Furthermore, the particular features, structures, or characteristics in one or more embodiments may include combined in any suitable manner.

Figure 1:
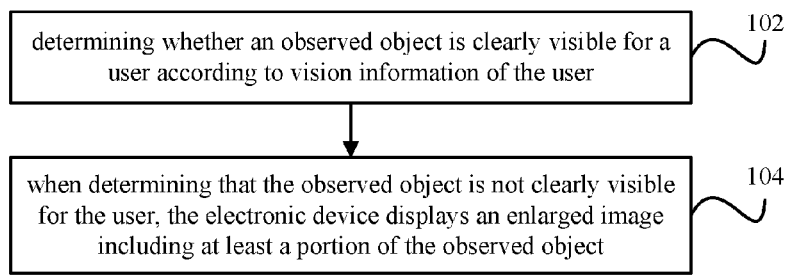
FIG. 1 is a flow chart showing a method for display control, according to an exemplary embodiment.

FIG. 1 is a flow chart showing a method for display control, according to an exemplary embodiment. Referring to FIG. 1, the method may include the following steps.

In step 102, determining whether an observed object is clearly visible for a user according to vision information of the user. The electronic device may acquire an image including one or more observed objects when a user wearing the electronic device looks around an area including the one or more observed objects.

In step 104, when determining that the observed object is not clearly visible for the user, the electronic device displays an enlarged image including at least a portion of the observed object.

There are a plurality of possible implementations for respective processing features in steps 102 and 104 in the technical solution of the present disclosure. Following are a few non-limiting examples to illustrate the processing features.

1. The Vision Information of the User

The vision information of the user refers to an ability of retinas of the user to distinguish an image. There are vision differences between different users, for example, some users may suffer from short sight, astigmatism or far sight, which may affect an observation of the observed object by the user.

The technical solution of the present disclosure may be applied in wearable devices, such as smart glasses. By determining the vision information of the user and the observed object, it may be automatically inferred whether the observed object can be clearly observed by the user, so as to perform a processing for automatically enlarging and displaying.

For convenience of illustration, the following embodiments all take the smart glasses for example. However, those skilled in the art will understand that, the technical solution of the present disclosure may be obviously applied in other unwearable electronic devices. Provided that the electronic device (such as a display screen) has a capability for processing information and displaying image, may identify the observed object and may determine an observing situation of the observed object by the user, the technical solution of the present disclosure may be applied.

1) Active Detection

As an exemplary embodiment, the smart glasses may actively perform an optometry on eyes of the user to acquire the vision information of the user.

Figure 2:
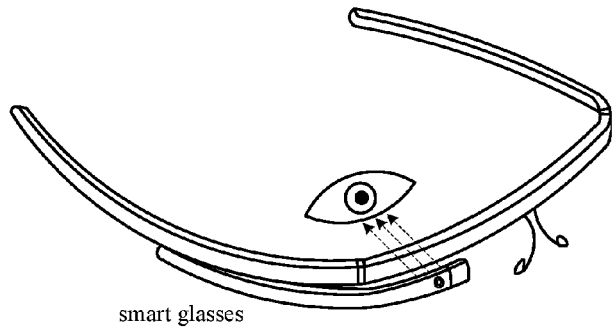
FIGS. 2-4 are schematic diagrams showing acquiring vision information of a user, according to an exemplary embodiment.

When the smart glasses performs the optometry on the user, a computer optometry in the related art may be used, a principle of which is "retinoscopy". As shown in FIG. 2, when the user wears the smart glasses, the smart glasses may project a beam of light into a refraction system of the eyes of the user, then to the retina directly via a retinoscope, and then a reflective light of the retina reaches the retinoscope, thus realizing a detection for the vision information.

During the optometry, a relaxation adjustment may be performed on eyeballs of the user by an infrared ray light source and an automatic scieropia device, and the refractive degree of the eyes of the user may be checked-up by photoelectric technology and automatic control technology.

Sure, obviously other manners may also be applied in the technical solution of the present disclosure besides the "retinoscopy", which are not limited by the present disclosure.

2) User Input

As another exemplary embodiment, the smart glasses may acquire the vision information according to received information inputted by the user, the information inputted by the user comprises the vision information.

When the user knows his or her vision, he or she may input his or her vision information directly. For example, an input interface for the vision information may be displayed on a display screen of the smart glasses. The input interface includes an input keyboard, and an eyeball movement of the user is captured so as to determine keys on the input keyboard focused by the vision of the user, thus accomplishing the information input.

Figure 3:
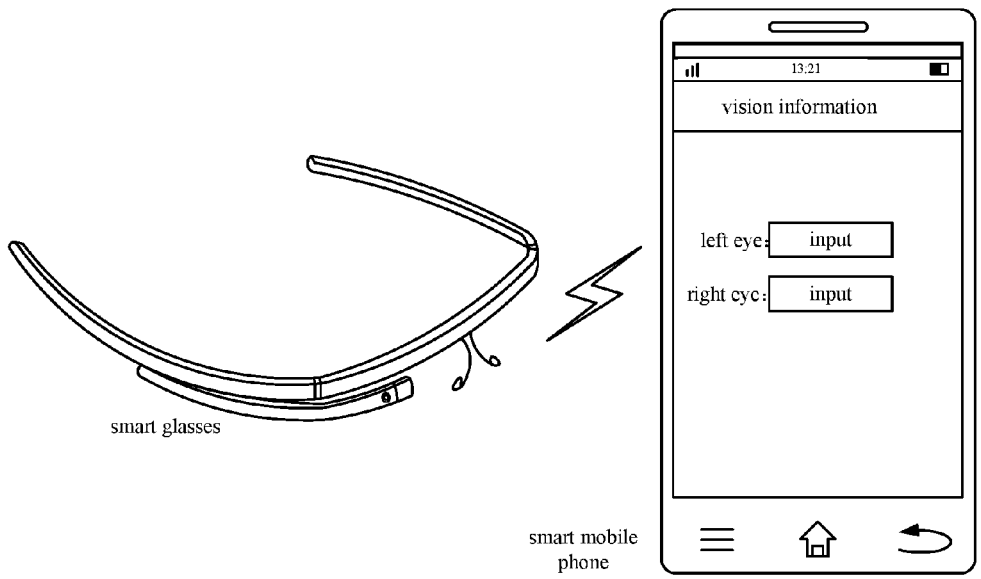

Alternatively, as shown in FIG. 3, the smart glasses may establish communication with other apparatus such as a smart mobile phone of the user, such that the user may directly input his or her vision information on an interface of the smart mobile phone as shown in FIG. 3.

3) Network Access

As yet another exemplary embodiment, the smart glasses may read the vision information associated with a login account of the user.

Figure 4:
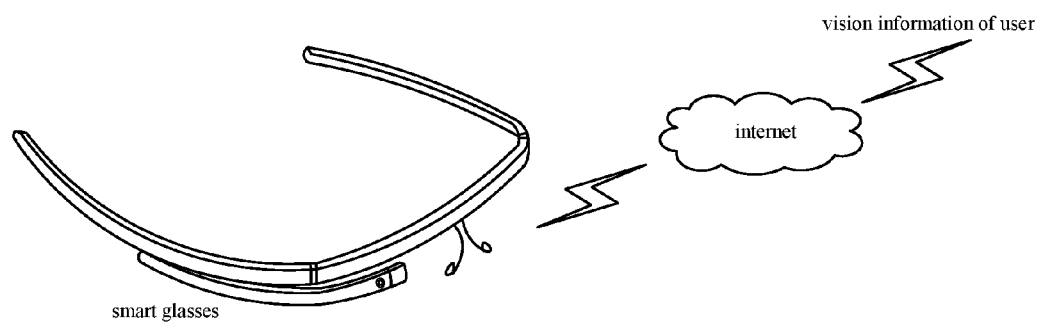

As shown in FIG. 4, the user may login an account on the smart glasses, and there is a one-to-one association between the account and the user. Thus, when the user stores his or her various information in the cloud in advance, such as the vision information, the height and the weight, the smart glasses may read the vision information of the user via an internet according to the current login account.

2. The Observed Object

Figure 5:
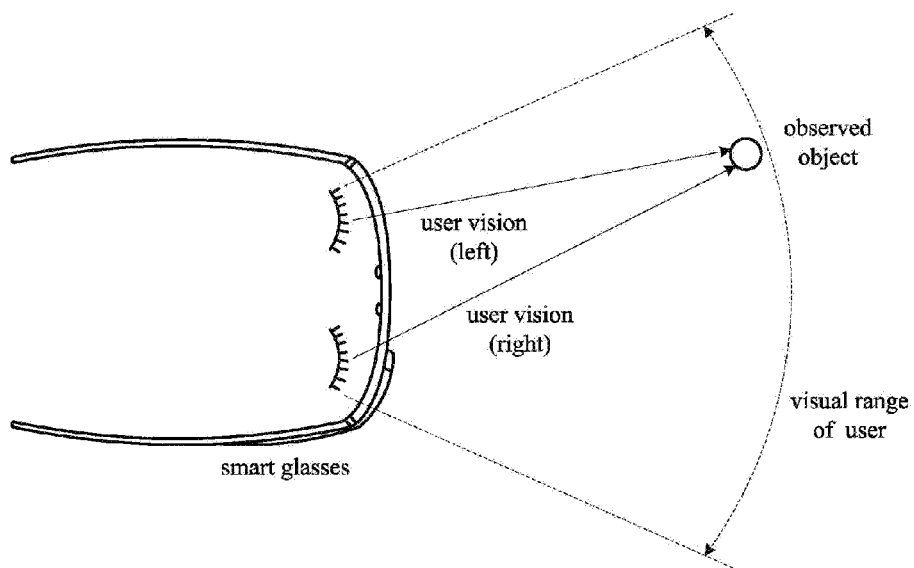
FIG. 5 is a schematic diagram showing determining an observed object according to an exemplary embodiment.

The "visual range of the user" may be understood as an observation range of the eyes of the user. As shown in FIG. 5, the visual range of the user is a sectorial area by overlook.

The smart glasses is located in front of the eyes of the user and consistent with an orientation of the eyes of the user, and may turn with a head of the user, and thus it may be considered that an image collection range of a camera on the smart glasses is generally consistent with the visual range of the user.

However, when the orientation of the head and the eyes of the user keep unchanged, although the visual range of the user may not change, a rotation of the eyeballs of the user may lead to a change of the observed object. Therefore, the smart glasses may capture a visual characteristic of the user by recording the rotation of the eyeballs of the user, so as to make an object matching the visual characteristic within the visual range of the user as the observed object.

For example, as shown in FIG. 5, by capturing a left eye vision and a right eye vision of the user, an object at an intersection between the left eye vision and the right eye vision is used as the observed object in the technical solution of the present disclosure.

3. Whether the User May Clearly Observe the Observed Object

1) Determination Based on Distance

As an exemplary embodiment, a spatial distance between the observed object and the user may be acquired, and determining whether the observed object is clearly visible for the user according to whether the spatial distance is greater than or equal to a predetermined visible distance.

Figure 6:
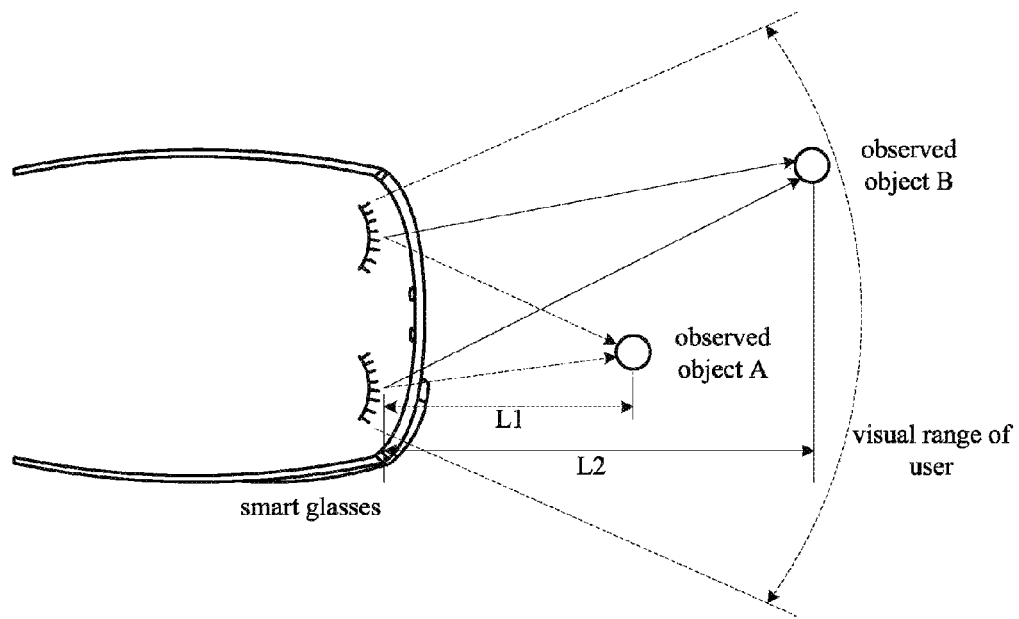
FIGS. 6-7 are schematic diagrams showing determining whether an observed object can be observed clearly by a user according to an exemplary embodiment.

As shown in FIG. 6, it is assumed that by capturing the visual characteristic of the user, the smart glasses determines an observed object A within the visual range of the user and measures a spatial distance L1 between the observed object A and the user; and the smart glasses determines an observed object B within the visual range of the user and measures a spatial distance L2 between the observed object B and the user.

When the user suffers from short sight, and it is determined that a farthest distance clearly observed by the user is L0 based on the visual information of the user, and L1<L0<L2, then it is determined that the observed object A may be clearly observed by the user without being enlarged display, while the observed object B cannot be clearly observed by the user such that the enlarged display is required.

Similarly, when the user suffers from far sight, and it is determined that a nearest distance clearly observed by the user is L0' based on the visual information of the user, and L1<L0'<L2., then it is determined that the observed object A cannot be clearly observed by the user such that the enlarged display is required, while the observed object B may be clearly observed by the user without enlarged display.

2) Determination Based on Detail

As another exemplary embodiment, determining whether the observed object is clearly visible for the user according to whether the observed object contains detailed information. When the observed object includes text, the observed object may be determined to be clearly visible when the text is legible to the user.

Figure 7:
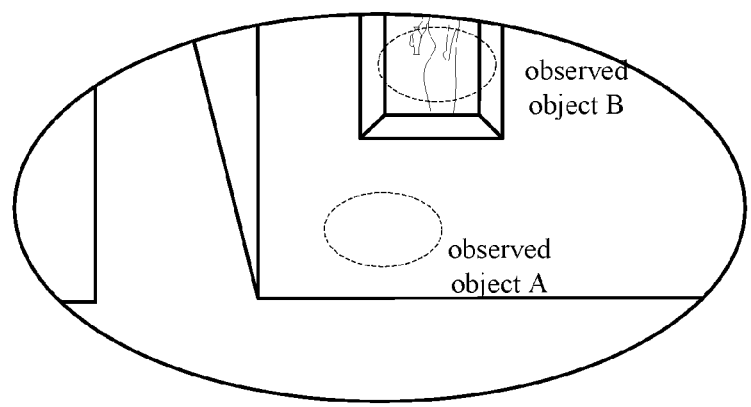

For example, when the observed object does not contain any detailed information, e.g., an observed object A shown in FIG. 7 that is a white wall, it actually makes nonsense for enlarged display. When the observed object contains detailed information, e.g., an observed object B shown in FIG. 7 that is a painting, it may be displayed in an enlarged size, such that it is convenient for the user to watch details of the painting. Therefore, the key point of the technical solution of this embodiment lies in how to determine the observed object contains the detailed information.

The smart glasses may acquire a variation degree of a predetermined pixel characteristic parameter of the observed object, and determine whether the observed object contains the detailed information according to whether the variation degree of the predetermined pixel characteristic parameter is greater than or equal to a predetermined variation degree.

In this embodiment, the pixel characteristic parameter may be one or more property values of each pixel, such as a gray value, a color value of each color channel. Take "the white wall" and "the painting" shown in FIG. 7 as example. For the former, all pixels of the image are "white", that is, corresponding gray values (the gray value is taken as example herein, other type of pixel characteristic parameter may also work) thereof are identical without any variation, such that it is determined that the observed object does not contain any detailed information. However, for the latter, since "the painting" contains lots of details, such as a color variation which may obviously result in difference and variation of the gray value of each pixel, even result in a large variation degree (e.g., greater than or equal to a predetermined variation degree), it is determined that the observed object contains the detailed information.

The smart glasses may acquire a surrounding object of the observed object, and determine whether the observed object contains the detailed information according to whether a variation degree of a predetermined pixel characteristic parameter of the observed object is consistent with that of the surrounding object. Here, the surrounding object includes an object within a preset distance from the observed object and the surrounding object and the observed object are in the same image obtained by the smart glass. Alternatively or additionally, the surrounding object may include a background object like a wall, a piece of furniture, etc.

In this embodiment, also take FIG. 7 as example. For the observed object A, because it belongs to a part of "the white wall", the variation degree of the predetermined pixel characteristic parameter of the observed object A is consistent with that of the surrounding object, that is, the observed object A and the surrounding object thereof form an entirety with large volume, there is no requirement for observing details for the user, and thus it may be determined that the observed object does not contain any detailed information. For the observed object B, since it is a painting on the white wall, the variation degree of the predetermined pixel characteristic parameter of the observed object B is not consistent with that of the surrounding object, and there is a large variation degree (e.g., greater than or equal to a predetermined variation degree), it is determined that the observed object contains the detailed information.

3) Determination Based on Time

As yet another exemplary embodiment, a duration time or a vision focus time of the user for observing a same object is acquired, and it is determined whether the observed object is clearly visible for the user according to whether the duration time or the vision focus time is greater than or equal to a predetermined time length.

In this embodiment, when the user observes or focuses on a certain observed object for a long time, it is indicated that the user may wish to look up the observed object carefully, or when the user tries to focus his or her vision because of failing to watch, it is indicated that the user wishes to observe the currently observed object in details, and thus the enlarged display is required.

4) Determination Based on Information Element

As yet another exemplary embodiment, it is determined whether the observed object is clearly visible for the user according to whether the observed object contains a predetermined type of information element. The information element may include a character, an icon, a Roman letter, a commodity logo, a traffic sign, a human face, etc. The user may also specify the information element during the initial setup of the smart glasses.

For example, after determining the currently observed object, the smart glasses may further identify the information element contained in the observed object. When the observed object contains such information element, it is determined that the observed object cannot be clearly observed by the user, and thus the enlarged display is required.

It will be noted that, although four manners have been introduced above, any one or a combination of the manners described above may be applied in practice, such that an accurate determination can be made on whether the observed object is clearly observed by the user. When the combination of various manners is applied, as an exemplary embodiment, it is determined that the observed object cannot be clearly observed by the user under a circumstance that a determination result of at least one method is that the observed object cannot be clearly observed by the user; or as another exemplary embodiment, it is determined that the observed object cannot be clearly observed by the user under a circumstance that determination results of all manners applied are that the observed object cannot be clearly observed by the user.

4. Displaying an Enlarged Image Including at Least a Portion of the Observed Object As an exemplary embodiment, a displaying region in a predetermined size may be displayed, and the enlarged image including at least a portion of the observed object may be displayed in the displaying region.

Figure 8:
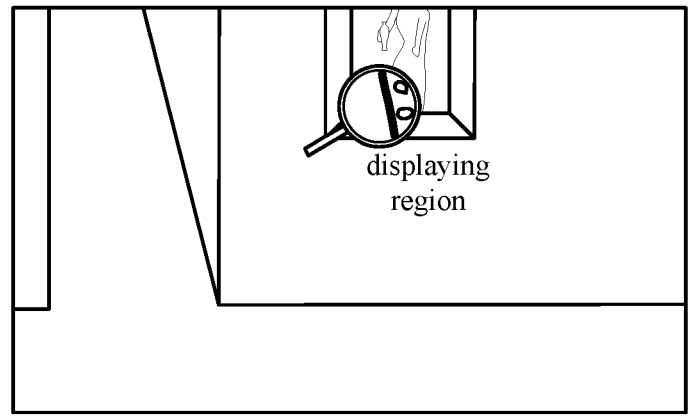
FIGS. 8-10 are schematic diagrams showing displaying an enlarged image of an observed object according to an exemplary embodiment.

It is assumed that FIG. 7 is a schematic diagram of imaging of the visual range of the user in the eyes of the user, and FIG. 8 is a schematic diagram showing the enlarged image including at least a portion of the observed object B displayed by the smart glasses. As shown in FIG. 8, the displaying region may be displayed in an image, and the displaying region may be "a magnifying glass" or other forms, which is not limited herein. It can be seen from FIG. 8 that, by the enlarged displaying of the observed object B, a dot pattern on a left side of a skirt of the person in the painting may be observed, while such details cannot be directly observed by the user.

Figure 9:
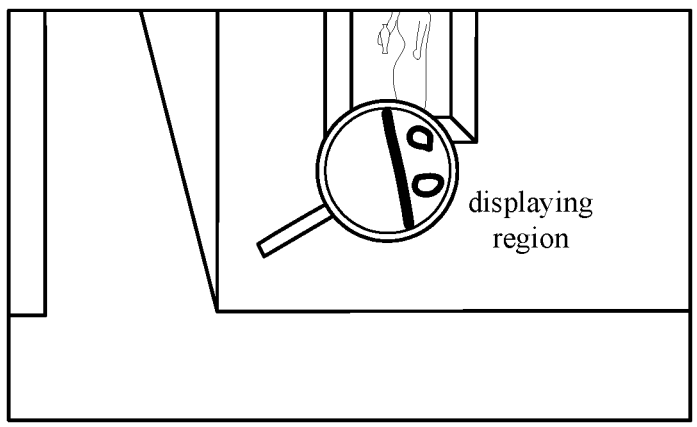

The user may control an enlargement scale of the observed object, for example, after the user sends an enlargement scale instruction to the smart glasses, a schematic diagram shown in FIG. 9 is obtained. Both a displaying content in the displaying region and a displaying content belonging to the observed object B in the displaying region are enlarged. Sure, only the displaying content in the displaying region may be enlarged. But an increase of the displaying region may ensure a large enough displaying area so as to facilitate an observation of the user.

Further, the smart glasses may monitor a vision shift event of the user and shift the displaying region according to the vision shift event, where the enlarged image including at least a portion of the observed object displayed in the displaying region is updated according to an enlargement scale of the enlarged image of the observed object. For example, as shown in FIG. 10, when the vision of the user shifts rightwards, the displaying region shifts accordingly, and the displaying content in the displaying region may also be updated, for example, "the left side of the skirt" shown in FIG. 9 is updated as "a right side of the skirt" shown in FIG. 10.

Here, when the vision of the user shifts out of a range of the observed object, the displaying of the enlarged image of the observed object will be cancelled, because "the observed object" here has been changed, a new observed object will be determined again according to the embodiments described above, and it is determined whether the new observed object will be displayed in an enlarged size.

Figure 10:
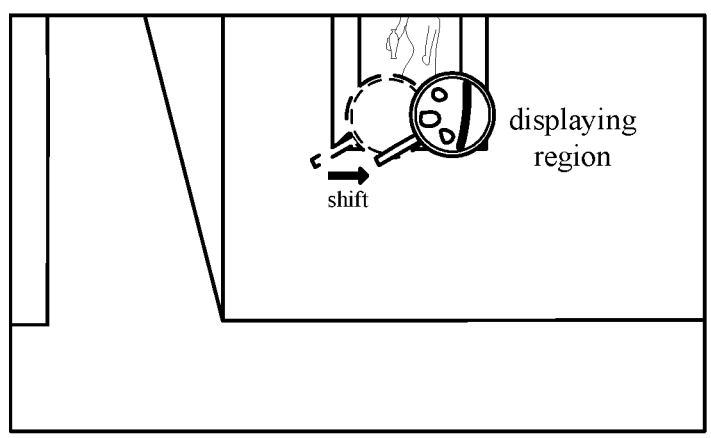

It will be noted that, "the displaying region" in form of "the magnifying glass" shown in FIGS. 8-10 is not necessary, the smart glasses may only enlarge and display the displaying content, and a whole display screen of the smart glasses may serve as "the displaying region."

Corresponding to the embodiments of the method for display control described above, the present disclosure further provides embodiments of an apparatus for display control.

Figure 11:
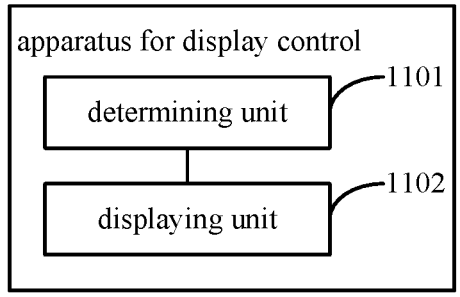
FIGS. 11-22 are block diagrams of an apparatus for display control according to an exemplary embodiment.

FIG. 11 is block diagram of an apparatus for display control according to an exemplary embodiment. Referring to FIG. 11, the apparatus includes a determining unit 1101 and a displaying unit 1102.

The determining unit 1101 is configured to determine whether an observed object is clearly visible for a user according to vision information of the user.

The displaying unit 1102 is configured to display an enlarged image of the observed object when it is determined that the observed object is not clearly visible for the user.

Figure 12:
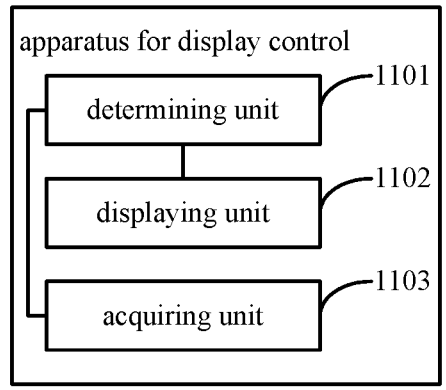

FIG. 12 is a block diagram of another apparatus for display control according to an exemplary embodiment. Based on the embodiment described above shown in FIG. 11, the apparatus may further include an acquiring unit 1103.

The acquiring unit 1103 is configured to acquire the vision information of the user by performing an optometry on eyes of the user to acquire the vision information; or according to received information inputted by the user, the information inputted by the user comprising the vision information; or by reading the vision information associated with a login account of the user.

Figure 13:
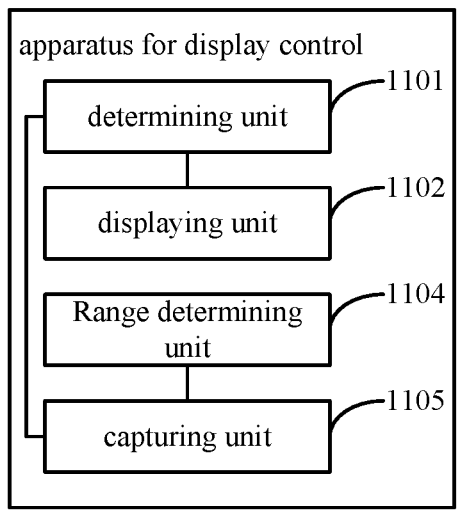

FIG. 13 is a block diagram of another apparatus for display control according to an exemplary embodiment. Based on the embodiment described above shown in FIG. 11, the apparatus may further include a range determining unit 1104 and a capturing unit 1105.

The range determining unit 1104 is configured to determine a current visual range of the user.

The capturing unit 1105 is configured to capture a visual characteristic of the user and to use an object matching the visual characteristic within the visual range of the user as the observed object.

It will be noted that, structures of the range determining unit 1104 and the capturing unit 1105 in the apparatus of the embodiment described above shown in FIG. 13 may also be included in the apparatus of the embodiment described above shown in FIG. 12, which is not limited in the present disclosure.

Figure 14:
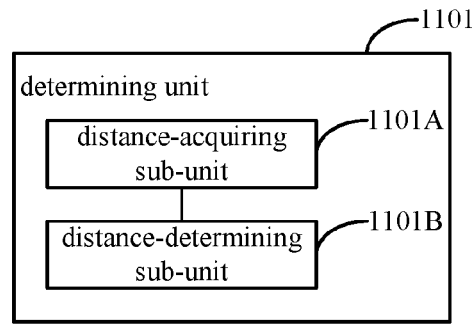

FIG. 14 is a block diagram of another apparatus for display control according to an exemplary embodiment. Based on the embodiment described above shown in FIG. 11, the determining unit 1101 may further include a distance-acquiring sub-unit 1101A and a distance-determining sub-unit 1101B.

The distance-acquiring sub-unit 1101A is configured to acquire a spatial distance between the observed object and the user.

The distance-determining sub-unit 1101B is configured to determine whether the observed object is clearly visible for the user according to whether the spatial distance is greater than or equal to a predetermined visible distance. When the spatial distance is greater than or equal to the predetermined visible distance, it is determined that the observed object is not clearly visible for the user.

It will be noted that, structures of the distance-acquiring sub-unit 1101A and the distance-determining sub-unit 1101B in the apparatus of the embodiment described above shown in FIG. 14 may also be included in the apparatus of the embodiments described above shown in FIGS. 12-13, which is not limited in the present disclosure.

Figure 15:
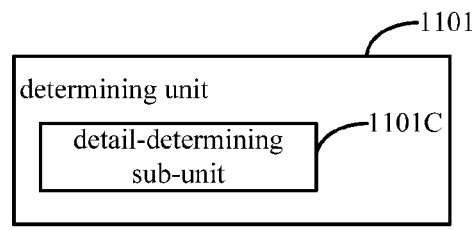

FIG. 15 is a block diagram of another apparatus for display control according to an exemplary embodiment. Based on the embodiment described above shown in FIG. 11, the determining unit 1101 may further include a detail-determining sub-unit 1101C.

The detail-determining sub-unit 1101C is configured to determine whether the observed object is clearly visible for the user according to whether the observed object contains detailed information. When the observed object contains the detailed information, determining that the observed object is not clearly visible for the user.

It will be noted that, the structure of the detail-determining sub-unit 1101C in the apparatus of the embodiment described above shown in FIG. 15 may also be included in the apparatus of the embodiments described above shown in FIGS. 12-14, which is not limited in the present disclosure.

Figure 16:
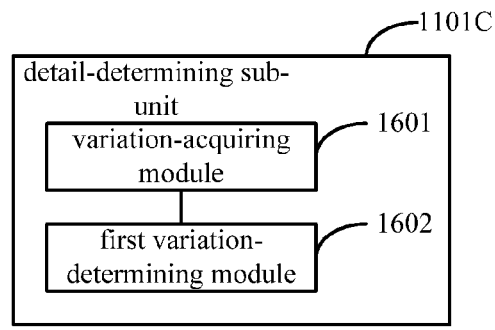

FIG. 16 is a block diagram of another apparatus for display control according to an exemplary embodiment. Based on the embodiment described above shown in FIG. 15, the detail-determining sub-unit 1101C may include a variation-acquiring module 1601 and a first variation-determining module 1602.

The variation-acquiring module 1601 is configured to acquire a variation degree of a predetermined pixel characteristic parameter of the observed object.

The first variation-determining module 1602 is configured to determine whether the observed object contains the detailed information according to whether the variation degree of the predetermined pixel characteristic parameter is greater than or equal to a predetermined variation degree.

When the variation degree of the predetermined pixel characteristic parameter is greater than or equal to the predetermined variation degree, it is determined that the observed object contains the detailed information.

Figure 17:
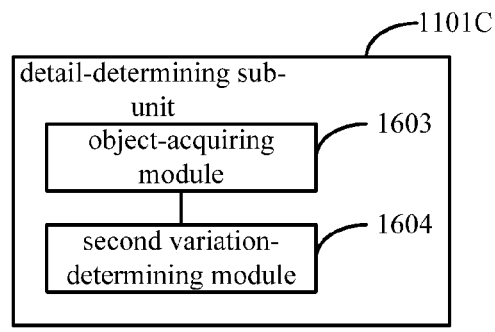

As shown in FIG. 17, FIG. 17 is a block diagram of another apparatus for display control according to an exemplary embodiment. Based on the embodiment described above shown in FIG. 15, the detail-determining sub-unit 1101C may include an object-acquiring module 1603 and a second variation-determining module 1604.

The object-acquiring module 1603 is configured to acquire a surrounding object of the observed object.

The second variation-determining module 1604 is configured to determine whether the observed object contains the detailed information according to whether a variation degree of a predetermined pixel characteristic parameter of the observed object is consistent with that of the surrounding object. When the variation degree of the predetermined pixel characteristic parameter of the observed object is not consistent with that of the surrounding object, it is determined that the observed object contains the detailed information.

Figure 18:
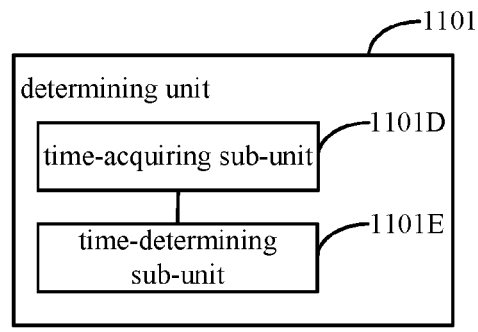

FIG. 18 is a block diagram of another apparatus for display control according to an exemplary embodiment. Based on the embodiment described above shown in FIG. 11, the determining unit 1101 may include a time-acquiring sub-unit 1101D and a time-determining sub-unit 1101E.

The time-acquiring sub-unit 1101D is configured to acquire a duration time or a vision focus time of the user for observing a same object.

The time-determining sub-unit 1101E is configured to determine whether the observed object is clearly visible for the user according to whether the duration time or the vision focus time is greater than or equal to a predetermined time length. When the duration time or the vision focus time is greater than or equal to the predetermined time length, it is determined that the observed object is not clearly visible for the user.

It will be noted that, structures of the time-acquiring sub-unit 1101D and the time-determining sub-unit 1101E in the apparatus of the embodiment described above shown in FIG. 18 may also be included in the apparatus of the embodiments described above shown in FIGS. 12-17, which is not limited in the present disclosure.

Figure 19:
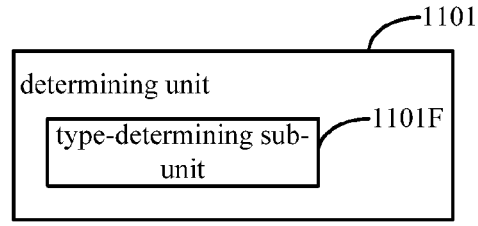

As shown in FIG. 19, FIG. 19 is a block diagram of another apparatus for display control according to an exemplary embodiment. Based on the embodiment described above shown in FIG. 11, the determining unit 1101 may include a type-determining sub-unit 1101F.

The type-determining sub-unit 1101F is configured to determine whether the observed object is clearly visible for the user according to whether the observed object contains a predetermined type of information element. When the observed object contains the predetermined type of information element, it is determined that the observed object is not clearly visible for the user.

It will be noted that, structures of the type-determining sub-unit 1101F in the apparatus of the embodiment described above shown in FIG. 19 may also be included in the apparatus of the embodiments described above shown in FIGS. 12-18, which is not limited in the present disclosure.

Figure 20:
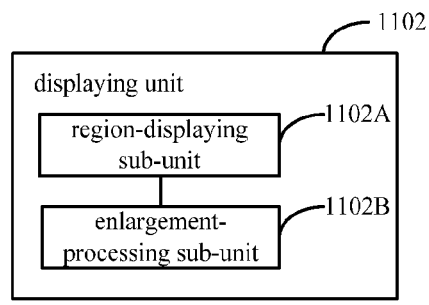

FIG. 20 is a block diagram of another apparatus for display control according to an exemplary embodiment. Based on the embodiment described above shown in FIG. 11, the displaying unit 1102 may include a region-displaying sub-unit 1102A and an enlargement-processing sub-unit 1102B.

The region-displaying sub-unit 1102A is configured to display a displaying region in a predetermined size.

The enlargement-processing sub-unit 1102B is configured to display the enlarged image of the observed object in the displaying region.

It will be noted that, structures of the region-displaying sub-unit 1102A and the enlargement-processing sub-unit 1102B in the apparatus of the embodiment described above shown in FIG. 20 may also be included in the apparatus of the embodiments described above shown in FIGS. 12-19, which is not limited in the present disclosure.

Figure 21:
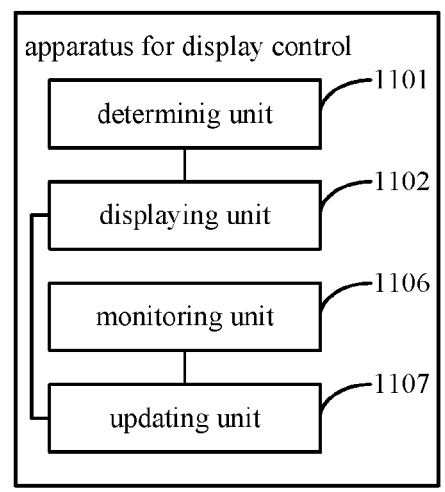

As shown in FIG. 21, FIG. 21 is a block diagram of another apparatus for display control according to an exemplary embodiment. Based on the embodiment described above shown in FIG. 20, the apparatus may further include a monitoring unit 1106 and an updating unit 1107.

The monitoring unit 1106 is configured to monitor a vision shift event of the user.

The updating unit 1107 is configured to shift the displaying region according to the vision shift event and to update the enlarged image of the observed object displayed in the displaying region according to an enlargement scale of the enlarged image of the observed object.

Figure 22:
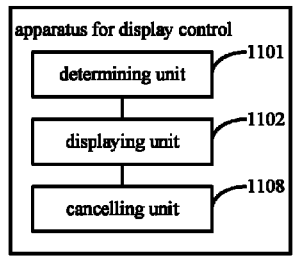

As shown in FIG. 22, FIG. 22 is a block diagram of another apparatus for display control according to an exemplary embodiment. Based on the embodiment described above shown in FIG. 11, the apparatus may further include a cancelling unit 1108.

The cancelling unit 1108 is configured to cancel the displaying of the enlarged image of the observed object, when a vision of the user shifts out of a range of the observed object.

It will be noted that, a structure of the cancelling unit 1108 in the apparatus of the embodiment described above shown in FIG. 22 may also be included in the apparatus of the embodiments described above shown in FIGS. 12-21, which is not limited in the present disclosure.

With respect to the apparatus in the above embodiments, the specific manners for performing operations for individual modules therein have been described in detail in the embodiments regarding the methods, which will not be elaborated herein.

Since the embodiments of the apparatus are basically corresponding to the embodiments of the method, as far as the embodiments of the apparatus, the correlations may refer to a partial illustration of the embodiments of the method. It is intended that the embodiments of the apparatus described above is exemplary only. The unit illustrated as a separated component may be or may not be physically separated, and the component appearing as a unit may be or may not be a physical unit, that is, the component may be located in one place or may be distributed on a plurality of network units. A partial or all of modules may be selected according to practical requirements to implement the aim of the solution of the present disclosure. It may be understood and implemented by those skilled in the art without creative work.

Accordingly, the present disclosure further provides a device for display control, including a processor and a memory for storing instructions executable by the processor. The processor is configured: to determine whether an observed object is clearly visible for a user according to vision information of the user; when the observed object is not clearly visible for the user, to display an enlarged image of the observed object.

Accordingly, the present disclosure further provides a terminal, including a memory and one or more programs. The one and more programs are stored in the memory and configured to be executed by one or more processors. The one and more programs include instructions for performing following operations: determining whether an observed object is clearly visible for a user according to vision information of the user; when the observed object is not clearly visible for the user, displaying an enlarged image of the observed object.

Figure 23:
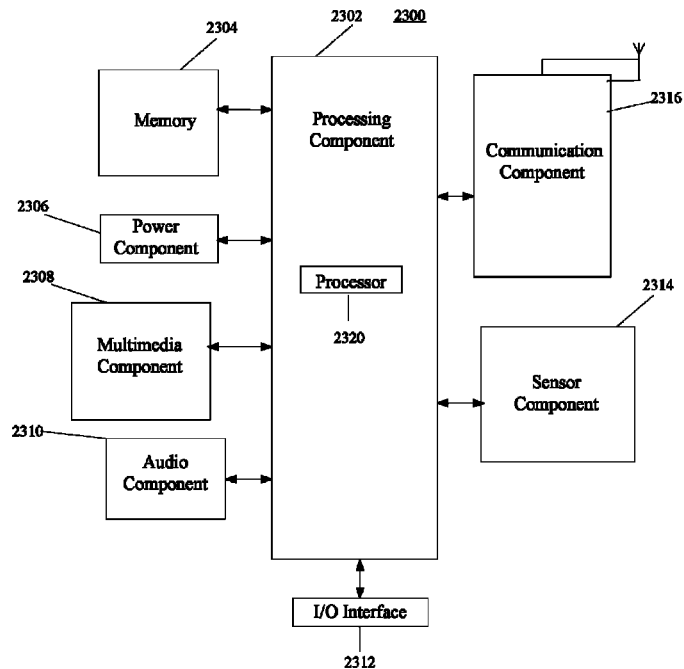
FIG. 23 is a schematic diagram of an apparatus for display control according to an exemplary embodiment.

FIG. 23 is a block diagram of a device 2300 for display control, according to an exemplary embodiment. For example, the device 2300 may be a mobile phone, a computer, a digital broadcast terminal, a messaging device, a gaming console, a tablet, a medical device, exercise equipment, a personal digital assistant, and the like.

Referring to FIG. 23, the device 2300 may include one or more of the following components: a processing component 2302, a memory 2304, a power component 2306, a multimedia component 2308, an audio component 2310, an input/output (I/O) interface 2312, a sensor component 2314, and a communication component 2316.

The processing component 2302 typically controls overall operations of the device 2300, such as the operations associated with display, telephone calls, data communications, camera operations, and recording operations. The processing component 2302 may include one or more processors 2320 to execute instructions to perform all or part of the steps in the above described methods. Moreover, the processing component 2302 may include one or more modules which facilitate the interaction between the processing component 2302 and other components. For instance, the processing component 2302 may include a multimedia module to facilitate the interaction between the multimedia component 2308 and the processing component 2302.

The memory 2304 is configured to store various types of data to support the operation of the device 2300. Examples of such data include instructions for any applications or methods operated on the device 2300, contact data, phonebook data, messages, pictures, video, etc. The memory 2304 may be implemented using any type of volatile or non-volatile memory devices, or a combination thereof, such as a static random access memory (SRAM), an electrically erasable programmable read-only memory (EEPROM), an erasable programmable read-only memory (EPROM), a programmable read-only memory (PROM), a read-only memory (ROM), a magnetic memory, a flash memory, a magnetic or optical disk.

The power component 2306 provides power to various components of the device 2300. The power component 2306 may include a power management system, one or more power sources, and any other components associated with the generation, management, and distribution of power in the device 2300.

The multimedia component 2308 includes a screen providing an output interface between the device 2300 and the user. In some embodiments, the screen may include a liquid crystal display (LCD) and a touch panel (TP). When the screen includes the touch panel, the screen may be implemented as a touch screen to receive input signals from the user. The touch panel includes one or more touch sensors to sense touches, swipes, and gestures on the touch panel. The touch sensors may not only sense a boundary of a touch or swipe action, but also sense a period of time and a pressure associated with the touch or swipe action. In some embodiments, the multimedia component 2308 includes a front camera and/or a rear camera. The front camera and/or the rear camera may receive an external multimedia datum while the device 2300 is in an operation mode, such as a photographing mode or a video mode. Each of the front camera and the rear camera may be a fixed optical lens system or have focus and optical zoom capability.

The audio component 2310 is configured to output and/or input audio signals. For example, the audio component 2310 includes a microphone ("MIC") configured to receive an external audio signal when the device 2300 is in an operation mode, such as a call mode, a recording mode, and a voice recognition mode. The received audio signal may be further stored in the memory 2304 or transmitted via the communication component 2316. In some embodiments, the audio component 2310 further includes a speaker to output audio signals.

The I/O interface 2312 provides an interface between the processing component 2302 and peripheral interface modules, such as a keyboard, a click wheel, buttons, and the like. The buttons may include, but are not limited to, a home button, a volume button, a starting button, and a locking button.

The sensor component 2314 includes one or more sensors to provide status assessments of various aspects of the device 2300. For instance, the sensor component 2314 may detect an open/closed status of the device 2300, relative positioning of components, e.g., the display and the keypad, of the device 2300, a change in position of the device 2300 or a component of the device 2300, a presence or absence of user contact with the device 2300, an orientation or an acceleration/deceleration of the device 2300, and a change in temperature of the device 2300. The sensor component 2314 may include a proximity sensor configured to detect the presence of nearby objects without any physical contact. The sensor component 2314 may also include a light sensor, such as a CMOS or CCD image sensor, for use in imaging applications. In some embodiments, the sensor component 2314 may also include an accelerometer sensor, a gyroscope sensor, a magnetic sensor, a pressure sensor, or a temperature sensor.

The communication component 2316 is configured to facilitate communication, wired or wirelessly, between the device 2300 and other devices. The device 2300 can access a wireless network based on a communication standard, such as WiFi, 2G; or 3G or a combination thereof. In one exemplary embodiment, the communication component 2316 receives a broadcast signal or broadcast associated information from an external broadcast management system via a broadcast channel. In one exemplary embodiment, the communication component 2316 further includes a near field communication (NFC) module to facilitate short-range communications. For example, the NFC module may be implemented based on a radio frequency identification (RFID) technology, an infrared data association (IrDA) technology, an ultra-wideband (UWB) technology, a Bluetooth (BT) technology, and other technologies.

In exemplary embodiments, the device 2300 may be implemented with circuitries including: one or more application specific integrated circuits (ASICs), digital signal processors (DSPs), digital signal processing devices (DSPDs), programmable logic devices (PLDs), field programmable gate arrays (FPGAs), controllers, micro-controllers, microprocessors, or other electronic components, for performing the above described methods. The modules, units, and sub-units may be implemented using a combination of the above circuitries.

In exemplary embodiments, there is also provided a non-transitory computer-readable storage medium including instructions, such as included in the memory 2304, executable by the processor 2320 in the device 2300, for performing the above-described methods. For example, the non-transitory computer-readable storage medium may be a ROM, a RAM, a CD-ROM, a magnetic tape, a floppy disc, an optical data storage device, and the like.

Other embodiments of the invention will be apparent to those skilled in the art from consideration of the specification and practice of the invention disclosed here. This application is intended to cover any variations, uses, or adaptations of the invention following the general principles thereof and including such departures from the present disclosure as come within known or customary practice in the art. It is intended that the specification and examples be considered as exemplary only, with a true scope and spirit of the invention being indicated by the following claims.

It will be appreciated that the present invention is not limited to the exact construction that has been described above and illustrated in the accompanying drawings, and that various modifications and changes can be made without departing from the scope thereof. It is intended that the scope of the invention only be limited by the appended claims.

What is claimed is:

1. A method for display control, comprising:
    acquiring, by an electronic device comprising a processor, an image including one or more observed objects;
    determining, by the electronic device, whether an observed object is clearly visible for a user according to vision information of the user and according to whether the observed object contains detailed information; and
    when the observed object contains the detailed information, determining that the observed object is not clearly visible for the user, displaying, by the electronic device on, an enlarged image including at least a portion of the observed object,
    wherein determining whether the observed object is clearly visible for the user according to whether the observed object contains detailed information comprises:
    acquiring, by the electronic device, a variation degree of a predetermined pixel characteristic parameter of the observed object, the predetermined pixel characteristic parameter including one or more pixel values in the observed object; and
    determining, by the electronic device, whether the observed object contains detailed information according to whether the variation degree of the predetermined pixel characteristic parameter is greater than or equal to a predetermined variation degree, wherein when the variation degree of the predetermined pixel characteristic parameter is greater than or equal to a predetermined variation degree, determining that the observed object contains the detailed information.

2. The method according to claim 1, further comprising acquiring the vision information of the user
    by performing an optometry on eyes of the user to acquire the vision information; or
    by receiving user input information comprising the vision information; or
    by reading the vision information associated with a login account of the user.

3. The method according to claim 1, further comprising:
    determining, by the electronic device, a current visual range of the user; and
    capturing, by the electronic device, a visual characteristic of the user and using an object matching the visual characteristic within the visual range of the user as the observed object.

4. The method according to claim 1, wherein determining whether the observed object is clearly visible for the user comprises:
    acquiring a spatial distance between the observed object and the user;
    determining whether the observed object is clearly visible for the user according to whether the spatial distance is greater than or equal to a predetermined visible distance, wherein when the spatial distance is greater than or equal to the predetermined visible distance, determining that the observed object is not clearly visible for the user.

5. The method according to claim 1, wherein determining whether the observed object is clearly visible for the user according to whether the observed object contains detailed information comprises:
    acquiring a surrounding object of the observed object; and
    determining whether the observed object contains detailed information according to whether a variation degree of a predetermined pixel characteristic parameter of the observed object is consistent with that of the surrounding object, wherein when the variation degree of the predetermined pixel characteristic parameter of the observed object is not consistent with that of the surrounding object, determining that the observed object contains the detailed information.

6. The method according to claim 1, wherein determining whether the observed object is clearly visible for the user comprises:
    acquiring, by the electronic device, a duration time of the user for observing the observed object; and
    determining, by the electronic device, whether the observed object is clearly visible for the user according to whether the duration time is greater than or equal to a predetermined time length, wherein when the duration time is greater than or equal to the predetermined time length, determining that the observed object is not clearly visible for the user.

7. The method according to claim 1, wherein determining whether the observed object is clearly visible for the user comprises:
    determining, by the electronic device, whether the observed object is clearly visible for the user according to whether the observed object contains a predetermined type of information element, wherein when the observed object contains the predetermined type of information element, determining that the observed object is not clearly visible for the user.

8. The method according to claim 1, wherein displaying an enlarge image including at least a portion of the observed object comprises:
    displaying a displaying region in a predetermined size;
    displaying the enlarged image including at least a portion of the observed object in the displaying region.

9. The method according to claim 8, further comprising:
    monitoring a vision shift event of the user; and
    shifting the displaying region according to the vision shift event, and updating the enlarged image displayed in the displaying region according to an enlargement scale of the enlarged image.

10. The method according to claim 1, further comprising:
    cancelling the displaying of the enlarged image, when determining that the user shifts vision out of a range of the observed object.

11. An electronic device, comprising:
a processor;
a memory for storing instructions executable by the processor;
wherein the processor is configured to:
determine whether an observed object is clearly visible for a user according to vision information of the user and according to whether the observed object contains detailed information; and
when the observed object contains the detailed information, determine that the observed object is not clearly visible for the user, display an enlarged image including at least a portion of the observed object,
wherein the processor is configured to determine whether the observed object is clearly visible for the user according to whether the observed object contains detailed information by:
acquiring a variation degree of a predetermined pixel characteristic parameter of the observed object, the predetermined pixel characteristic parameter including one or more pixel values in the observed object; and
determining whether the observed object contains detailed information according to whether the variation degree of the predetermined pixel characteristic parameter is greater than or equal to a predetermined variation degree, wherein when the variation degree of the predetermined pixel characteristic parameter is greater than or equal to a predetermined variation degree, determining that the observed object contains the detailed information.

12. The electronic device according to claim 11, wherein the processor is further configured to acquire the vision information of the user
by performing an optometry on eyes of the user to acquire the vision information; or
by receiving user input information comprising the vision information; or
by reading the vision information associated with a login account of the user.

13. The electronic device according to claim 11, wherein the processor is further configured to:
determine a current visual range of the user; and
capture a visual characteristic of the user and using an object matching the visual characteristic within the visual range of the user as the observed object.

14. The electronic device according to claim 11, wherein the processor is configured to determine whether the observed objet is clearly visible for the user by:
acquiring a spatial distance between the observed object and the user;
determining whether the observed object is clearly visible for the user according to whether the spatial distance is greater than or equal to a predetermined visible distance, wherein when the spatial distance is greater than or equal to the predetermined visible distance, determining that the observed object is not clearly visible for the user.

15. The electronic device according to claim 11, wherein the processor is configured to determine whether the observed object is clearly visible for the user according to whether the observed object contains detailed information by:
acquiring a surrounding object of the observed object; and
determining whether the observed object contains detailed information according to whether a variation degree of a predetermined pixel characteristic parameter of the observed object is consistent with that of the surrounding object, wherein when the variation degree of the predetermined pixel characteristic parameter of the observed object is not consistent with that of the surrounding object, determining that the observed object contains the detailed information.

16. A non-transitory computer-readable storage medium having stored therein instructions that, when executed by a processor of a terminal device, causes the terminal to perform acts comprising:
determining whether an observed object is clearly visible for a user according to vision information of the user and according to whether the observed object contains detailed information; and
when the observed object contains the detailed information, determining that the observed object is not clearly visible for the user, displaying an enlarged image including at least a portion of the observed object,
wherein determining whether the observed object is clearly visible for the user according to whether the observed object contains detailed information comprises:
acquiring a variation degree of a predetermined pixel characteristic parameter of the observed object, the predetermined pixel characteristic parameter including one or more pixel values in the observed object; and
determining whether the observed object contains detailed information according to whether the variation degree of the predetermined pixel characteristic parameter is greater than or equal to a predetermined variation degree, wherein when the variation degree of the predetermined pixel characteristic parameter is greater than or equal to a predetermined variation degree, determining that the observed object contains the detailed information.

* * * * *